United States Patent [19]
Lualdi et al.

[11] Patent Number: 6,162,905
[45] Date of Patent: Dec. 19, 2000

[54] FSH AND LH SEPARATION AND PURIFICATION PROCESS

[75] Inventors: Paolo Lualdi, Grandate; Elisabetta Donati, Cavallasca, both of Italy; Irina Rapaport, Rovio, Switzerland

[73] Assignee: IBSA Institut Biochimique S.A., Lugano, Switzerland

[21] Appl. No.: 09/111,090

[22] Filed: Jul. 6, 1998

[30] Foreign Application Priority Data

Nov. 7, 1996 [IT] Italy ................................. MI96A2313
Nov. 3, 1997 [WO] WIPO ...................... PCT/EP97/06058

[51] Int. Cl.[7] ................................. C07K 1/14; C07K 1/16; C07K 1/36; C07K 1/22
[52] U.S. Cl. ......................... 530/412; 530/413; 530/416; 530/418; 530/422; 530/424; 530/399
[58] Field of Search .................................... 530/412, 413, 530/416, 418, 424, 422, 399

[56] References Cited

U.S. PATENT DOCUMENTS

| | | | |
|---|---|---|---|
| 3,674,865 | 7/1972 | Domini | 424/99 |
| 3,973,004 | 8/1976 | Volynsky | 424/108 |
| 4,115,375 | 9/1978 | Pedersen | 260/112.5 |
| 4,665,161 | 5/1987 | Yuki et al. | 530/412 |

FOREIGN PATENT DOCUMENTS

| | | |
|---|---|---|
| 089 218 | 9/1983 | European Pat. Off. . |
| 328248 | 8/1989 | European Pat. Off. . |
| 322438 | 12/1994 | European Pat. Off. . |
| 8501958 | 5/1985 | WIPO . |

*Primary Examiner*—F. T. Moezie
*Attorney, Agent, or Firm*—Hedman, Gibson & Costigan, P.C.

[57] ABSTRACT

A new process, particularly simple and economical, for FSH and LH separation and purification starting from crude HMG preferably urinary, comprising the following steps:

1) optional exhaustion of crude HMG viral charge in aqueous EtOH
2) ion-exchange chromatography on weakly basic anionic resins of DEAE type;
3) affinity chromatography on resin having an antraquinone derivative as a ligand;
4) optional ion-exchange chromatography on strongly basic anionic resins;

Hormones obtained thereby, in particularly pure form and having high specific activity, may subsequently undergo a depyrogenation step.

14 Claims, 6 Drawing Sheets

FSH AND LH SEPARATION AND PURIFICATION PROCESS

The present application is the national stage filing of and claims priority to International Application No. PCT/EP97/06058, filed Nov. 3, 1997 and Italian Application Serial No. MI96A002313.

FIELD OF THE INVENTION

The present invention refers to a new process, particularly simple and economical, for FSH and LH separation and purification starting from crude HMG, and particularly from urine extracts of menopausal or post-menopausal women.

STATE OF THE ART

Follicle Stimulating Hormone (FSH) and Luteinizing Hormone (LH) are usually known as gonadotropic hormones or human fertility hormones. Such compounds, whose primary physiological effect is directed to the promotion of gametogenesis and/or the production of steroids involved in such biological process, are abundantly available in nature from pituitary glands and human and animal plasma, as well as of the urine of menopausal or post-menopausal women. FSH and LH are drawn from such natural sources in the form of a mixture, commonly known as HMG (Human Menopausal Gonadotropin), which is available on the market also as a crude extract; this mixture consists of FSH and LH in a ratio of about 1:1 in association with other urinary proteins. Nevertheless, these extracts have low purity degrees, that are incompatible with their administration in men for therapeutic purposes, principally because of the contamination from foreign proteins.

Several FSH and LH purification processes starting from products of natural origin (pituitary glands, plasma or urine), essentially based on centrifugation, precipitation, chromatography and filtration techniques, have been developed in the state of the art with the aim of reducing the above mentioned protein contamination.

The U.S. Pat. No. 3,674,865 describes FSH purification from urinary extracts such process, comprising 21 different steps in total, still results into a mixture of FSH and LH in a ratio ranging between 3:1 and 6:1.

The U.S. Pat. No. 3,973,004 (Derwent abstract) describes FSH separation from pituitary glands by means of selective precipitation with ammonium sulphate, while in U.S. Pat. No. 4,115,375 (Claims U.S. patent abstract), polyethylene glycol is used as precipitant agent.

Nevertheless, the above mentioned processes suffer the disadvantage of leading to the obtainment of products having unsatisfactory specific activity and purity. In particular, the presence of protein contamination induces allergic reactions, so that the above mentioned hormones may be taken only by means of particular routes of administration, such as intramuscular injection, involving considerable difficulties in application.

In the recent past, some purification processes using immuno-affinity chromatography and specific monoclonal anti-bodies (European patent EP 0 322 438; European patent application EPA 0 328 248, Derwent abstract) or recombinant DNA techniques (international patent application WO 85/01958) have been set up. Though they allow to get products with high specific activity, these processes suffer the severe problem of possible contaminations from viruses, heterologous proteins and DNA residuals from the host cell; that is why products resulting from such processes have to be carefully purified and tested to exclude the presence of potential contaminants prior to their therapeutic use.

Therefore, there is an obvious need of a process which allows the obtainment of higher purity and higher specific activity products, without meeting the disadvantages mentioned above.

SUMMARY OF THE INVENTION

It is the object of the present invention to provide a FSH and LH separation and purification process, starting from crude HMG, allowing the obtainment of these hormones with high purity and specific activity. Said process comprises the following steps: optional exhaustion of the viral charge of said crude HMG in a 80–90% v/v EtOH water solution;

loading of the product obtained in step (1) on a ion-exchange chromatography column with weakly basic anionic resin of DEAE type, selectively eluting LH and FSH with 5–15% v/v EtOH aqueous solutions in a 10–50 mM phosphate buffer, containing 0–70 mM NaCl with increasing ionic strength, pH 7,0 to 8,0;

loading of the eluate obtained in step (2), containing LH or FSH, on an affinity chromatography column having a ligand consisting of an anthraquinone derivative on an inert support, selectively eluting contaminating proteins and FSH or LH with alkaline pH solutions, having an increasing ionic strength from 0 to 3 M of KCl;

optional loading of the FSH hormone obtained in step (3) on a ion-exchange chromatography column with strongly basic anionic resins, containing quaternary ammonium groups, selectively eluting contaminating proteins and FSH with 0–400 M NaCl solutions with increasing ionic strength, at alkaline pH.

Further to that, FSH and LH hormones, obtained in the above mentioned steps (3) and (4), may be depyrogened and lyophilized or frozen.

DETAILED DESCRIPTION OF THE INVENTION

Figure 1:
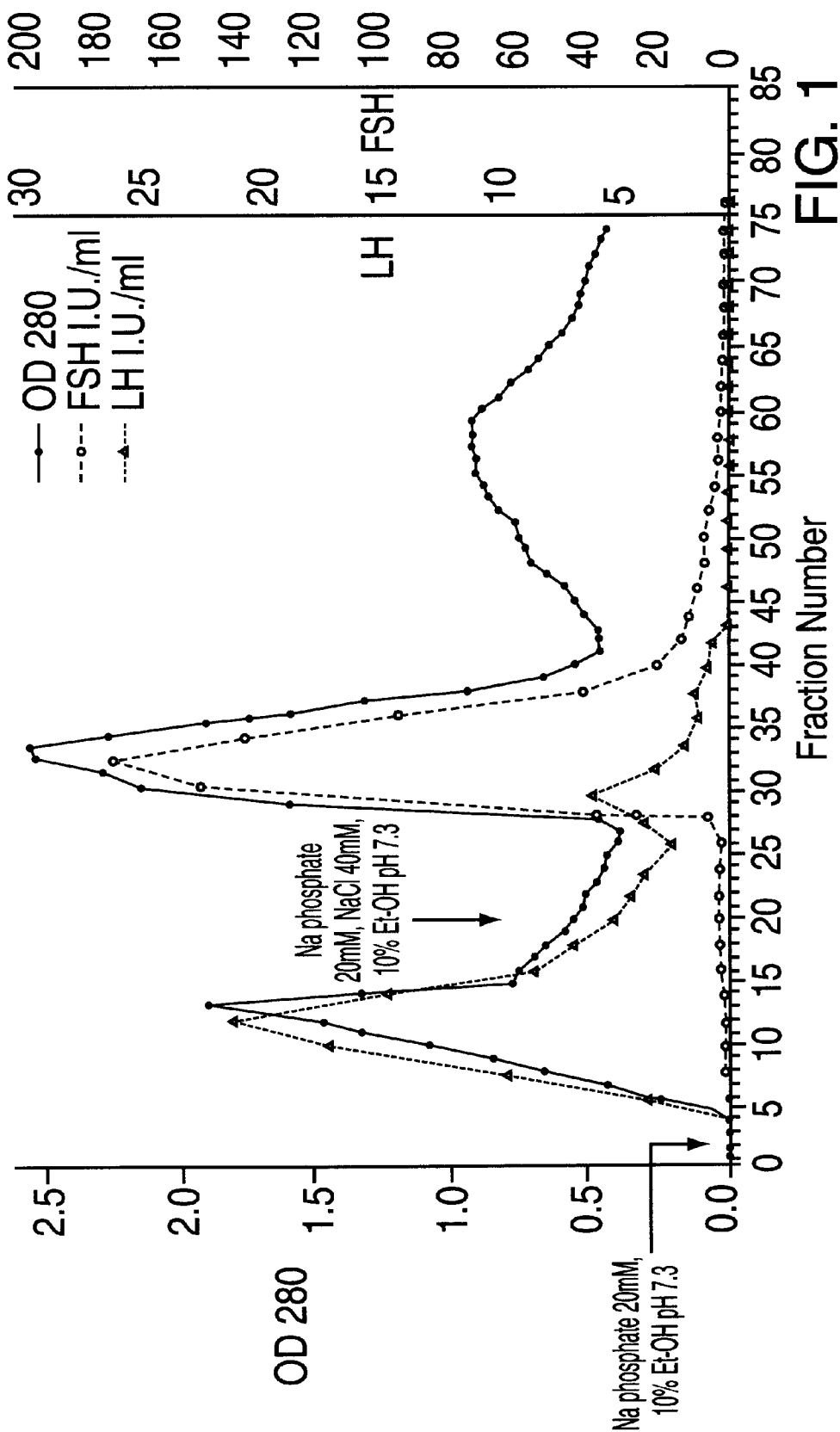

The characteristics and advantages of the process according to the present invention will be better reported in the following detailed description.

By means of a simple extraction and easy purification steps on ion-exchange and affinity resins, the process of the invention allows the obtainment of FSH and LH having high specific activity and high purity, thus allowing their administration to men for therapeutic purposes, with no need of further purification treatments. This process is particularly simple and economical, and it also has the advantage of using very limited quantities of organic solvents, since it is mainly carried out in water.

Starting crude HMG is preferably of an urinary concentrate obtained from the urine of menopausal or post-menopausal women; according to a preferred form of realization of the invention, said starting HMG has a specific activity in FSH lower than 10 I.U./mg, and more preferably ranging from 2 and 10 I.U./mg, and a specific activity in LH ranging from 0.5 and 5 I.U./mg.

In step (1) of the process of the invention, said crude HMG is suspended in a 80–90% v/v EtOH water solution, at a temperature preferably comprised between −20° C. and 5° C., for a period of 1 to 4 hours.

This treatment is carried out for the purpose of getting the exhaustion of crude HMG viral charge, which is essential to any use in the pharmaceutical field after purification.

In step (2) of the process of the invention, the solid residue, whose viral charge has been optionally exhausted in step (1) is solubilized in a 5–15% v/v EtOH water so solution in a 5–50 mM phosphate buffer, preferably containing 10–30 mM sodium phosphate, the pH ranging from 7.3 to 7.6, at a temperature ranging from 0° C. to 8° C. and preferably from 0° C. to 6° C.

The thus obtained solution is loaded on a ion-exchange chromatography column with weakly basic anionic resin of DEAE type, at a temperature preferably ranging from 0° C. to 8° C., preferably using a conditioning buffer consisting of a 5–15% v/v EtOH water solution containing a 5–50 mM phosphate buffer, preferably containing 10–30 mM sodium phosphate, at a pH of 7.3–7.6. Said anionic resin preferably contains tertiary aminic groups, optionally in the presence of quaternary ammonium groups, on cellulose matrix, and more preferably it is DEAE-cellulose (for example DE52 Whatman).

The preferred flow rate ranges from 10 to 30 ml/cm$^2$.h, with a column diameter/length ratio ranging from 0.3 and 0.6, and with a total protein load ranging from 20 to 50 mg/ml of resin.

LH hormon adsorbed on resin is preferably eluted with a 5–15% v/v EtOH water solution in a 10–50 mM phosphate buffer, preferably containing 10–30 mM sodium phosphate, at a pH of 7.3 and 7.6. Said elution, that results into the recovery of LH only, is preferably carried out at the temperature between of 0–8° C.

FSH hormone adsorbed on resin is subsequently eluted with a 5–15% v/v EtOH water solution in a 10–50 mM phosphate buffer, preferably containing 10–30 mM sodium phosphate, at a pH of 7.3–7.6, containing NaCl in concentration ranging from 30 to 50 mM. Said elution is preferably carried out the temperature of 0–8° C. The presence of EtOH in eluting buffer solutions plays a determining role in this step, because it enables a better LH and FSH separation, as well as higher yelds in the recovery of the two hormones.

In step (3) of the process of the invention, the eluates containing LH and FSH hormones, obtained from step (2), separately undergo a further purification procedure, by means of affinity chromatography containing an anthraquinone derivative as ligand, preferably CIBA-CRON® Blue, covalently linked to an inert support, preferably agarose, it is preferably used an affinity chromatography column consisting of agarose blue.

Said eluates are preferably acidified up to a pH of 5.5 and 7.5 and loaded onto the to above mentioned column, previously conditioned in a 10–30 mM acetate buffer, preferably containing sodium acetate, at a pH of 5.5 to 7.5, at a temperature ranging from 0° C. to 8° C.

The preferred flow rate ranges from 7 to 14 ml/cm$^2$.h, with a column diameter/length ratio ranging from 0.5 to 0.9, with a total protein load ranging from 5 to 15 mg/ml of resin.

The FSH or LH hormone, adsorbed on the column, is then selectively eluted from contaminating proteins with one or more 40–60 mM glycine-NaOH buffers, containing KCl in concentrations ranging from 0 to 3 M, optionally of increasing growing ionic strength, changing the pH from 8.5 to 11.

The thus obtained hormones may then be concentrated and desalified for a subsequent freezing or lyophilization, with procedures known in the state of the art.

According to a preferred form of realization of the process of the invention, desalified LH hormone is lyophilized and may subsequently undergo depyrogenation, with procedures known in the state of the art.

According to step (4), the FSH hormone obtained in step (3), once desalified, undergoes a further purification stage carried out by means of ion-exchange chromatography on strongly basic anionic resin; such resin contains quaternary ammonium groups, optionally in association with tertiary amminic groups, on cellulose matrix, and it is preferably DE53 Whatman.

FSH is preferably balanced by dialysis in a 10–50 mM Tris-HCl buffer, pH 9.0–9.5, and loaded on said column, conditioned with the same buffer.

The preferred flow rate ranges from 20 to 40 ml/cm$^2$.h, with a column diameter/lenght ratio ranging from 0.08 to 0.3, with a total protein load ranging from 0.5 to 10 mg/ml of resin.

Initially the column is eluted with a 10–50 mM Tris-HCl buffer, pH 9.0–9.5, containing NaCl in a concentration preferably ranging from 40 to 80 mM, thus obtaining the elution of contaminating proteins.

The FSH hormone bound to the resin is subsequently eluted using a linear NaCl concentration gradient, preferably ranging from 70–100 mM to 140–400 mM, in a 10–50 mM Tris-HCl buffer, pH 9.0–9.5.

The thus obtained, purified FSH hormone is then desalified by ultrafiltration, lyophilized and depyrogened with procedures known in the state of the art. According to a preferred embodiment of the invention, the process of depyrogenation of FSH and LH, obtained in steps (3) or (4), is carried out as follows: the purified hormone, in the form of lyodhiilzed powder, is dissolved, at a temperature comprised between −15° C. and 0° C., in a 30–50% v/v EtOH water solution, containing 5–15% w/v ammonium acetate.

To this solution are then added 3–8 mM tribasic sodium phosphate and 3–8 mM calcium acetate; the pH is then rised up to values ranging from 8 to 10 by means of sodium hydroxide. To the obtained supernatant, after centrifugation, 1,5–2,5 volumes of absolute EtOH for each supernatant volume are added at a temperature ranging between −20° C. and 0° C. After having carried out a further centrifugation, the obtained precipitate is dissolved again in water and dialyzed, according to methods known in the state of the art.

Finally, the solution containing purified LH or FSH may be frozen like it is or lyophilized according to methods known in the state of the art, thus keeping hormone activity unchanged for long-term storage.

The process of the invention enables the achievement of very high purity FSH and LH, and respectively of FSH having a specific activity exceeding 6,000 I.U./mg, free from LH, and of LH having a specific activity exceeding 500 I.U./mg.

The following examples of the present invention are reported for illustrative but not limitative purposes.

EXAMPLE 1

FSH Purification from Crude Urinary HMG

Exhaustion of the Viral Charge of Crude HMG in Aqueous EtOH

All the operations mentioned hereinafter were carried out at a temperature ranging from 0 to 6° C., unless differently specified.

200 g of crude HMG, obtained from the urine of menopausal or post-menopausal women, were suspended in 10 l of an ethanol/water mixture (85:15 v/v), at the temperature of −10° C.; the thus obtained suspension was maintained under stirring for 3 hours, at the temperature of −10° C., and then centrifuged at 7,000 rpm for 20 minutes, using a GS3 Sorvall rotor; after removal of the supernatant, the precipitate was recovered.

Ion-exchange Chromatoaraphy on DE52

The precipitate obtained in step 1.1 was dissolved in 2 l of a 10% EtOH solution, containing 20 mM sodium phospate, with a pH of 7,3. The thus obtained solution was centrifuged at 7,000 rpm for 30 minutes, using a GS3 Sorvall rotor, and the obtained supernatant was loaded on a DE52 Whatman ion-exchange column (1995 Catalogue Ref. 4057910), based on diethylaminoethylcellulose having a diameter of 14 cm and a height of 36 cm, balanced in a 20 mM sodium phosphate buffer, at pH of 7.3, containing the 10% v/v of EtOH. In the course of chromatography, the column was eluted at a flow rate of 3 l/hour and the eluate was collected in fractions of about 700 ml.

After the sample was loaded, the column was eluted with, in the order:

10 l of 10% v/v EtOH, containing 20 mM sodium phosphate, pH=7.3;

40 l of 10% v/v EtOH, containing 20 mM sodium phosphate and 40 mM sodium chloride, pH=7.3;

After chromatography, the optical density at 280 nm (OD280) was determined for each eluate fraction, as well as LH and FSH activities. FIG. 1 shows the obtained chromatogram, where are reported LH and FSH specific activities (I.U./ml) and the optical density of the eluate fractions.

Such chromatogram clearly shows that LH was eluted by buffer solution (a), while FSH was eluted by buffer solution (b), containing 40 mM NaCl. In particular, fractions from 6 to 20, containing LH, were collected and furtherly purified, as described in Example 2; fractions from 28 to 41, containing FSH, were collected and purified as described below.

FSH Purification by Means of Affinity Chromatography on Agarose Blue

The agarose blue 3 GA affinity resin (Sigma Chemical Co., St. Louis, Mo., 1995 Catalogue Ref. C1410) was used; this resin, prior to be packed into the chromatography column, was washed with following reagents:

10 l of a 2.5 M KCl solution in 0.5% $Na_2CO_3$ for one hour;

10 l of a 0.5% $Na_2CO_3$ solution for 30 minutes;

10 l of a 6 M urea solution for 2 hours;

10 l of $H_2O$ for 30 minutes;

10 l of a 0.5% $Na_2CO_3$ solution for 30 minutes;

10 l of $H_2O$ for 30 minutes;

10 l of a 50 mM sodium acetate buffer, pH=6.5, for 30 minutes;

10 l of a 20 mM sodium acetate buffer, pH=6.5, for 30 minutes.

The resin, conditioned in a 20 mM sodium acetate buffer, pH=6.5, was packed in a chromatography column to obtain a resin bed with a diameter of 11 cm and a height of 16 cm.

The pH of the sample containing FSH, obtained in step 1.2, was changed to 6.5 by means of 1.7 M acetic acid and loaded into the column.

Sample loading into the column and its further elutions were carried out at a flow rate of 1 l/h flow. The eluate recovered during the loading of the sample into the column was collected in one single fraction, while further fractions of about 700 ml were subsequently collected.

Figure 2:
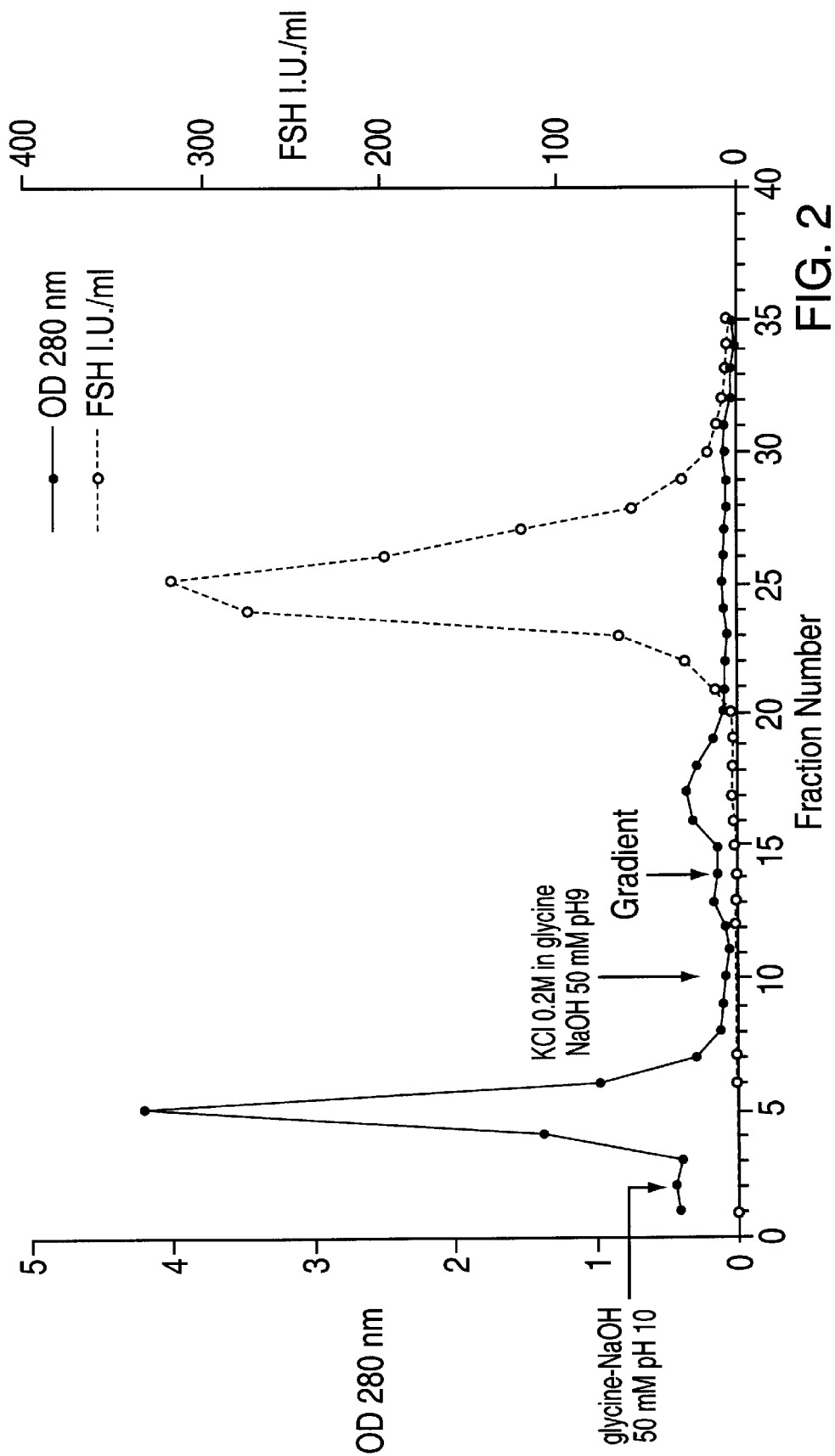

After having loaded the sample, the column was first eluted with, in the order:

1 l of a 20 mM sodium acetate buffer, pH=6.5;

5 l of a 50 mM glycine-NaOH buffer, pH=10;

3 l of a 50 mM glycine-NaOH, 0,2 M KCl buffer, pH=9; and then with a KCl linear gradient in a glycine-NaOH buffer, prepared as follows:

chamber 1) 9 l of 0.3 M KCl in 50 mM glycine-NaOH buffer, pH=9;

chamber 2) 9 l of 2.5 M KCl in 50 mM glycine-NaOH buffer, pH=9;

After chromatography, the optical density at 280 nm (OD280) of every eluate fraction, as well as FSH specific activity (I.U./ml), were determined. FIG. 2 shows the obtained chromatogram.

During sample loading (not reported in the graphic), FSH was retained in the column while the largest part of contaminating proteins was found in the eluate. Many of the contaminating proteins retained by the resin were eluted by the first washings and by the buffer containing 0.3 M KCl, while no FSH elution was observed under these conditions.

The subsequent elution (starting from fraction 14) with KCl gradient resulted first into the elimination of other contaminating proteins (from fraction 15 to fraction 20 approximately); FSH elution occurred with a symmetrical peak at higher KCl concentrations (fractions from 22 to 29).

After that, fractions from 23 to 28 were collected together; the pH of the obtained product was raised up to 7.5 with 1.7 M acetic acid; then the product itself way concentrated and desaiified by ultrafiltration, using an Amicon cell provided with an Amicon PM10 membrane.

Ion-exchange Chromatography on DE53

FSH sample, previously concentrated and desaiified as described in step 1.3, was dialyzed for 18 hours against 5 l of a 25 mM Tris-HCl buffer, pH=9.3; after that, the sample was loaded on a DE53 Whatman ion-exchange chromatography column (1995 Catalogue ref. 4058910), having a diameter of 2 cm and a height of 18 cm, balanced with a 25 mM Tris-HCl buffer, pH=9.3. The column was eluted with a flow rate of 100 ml/h and the eiuate was collected in fractions of about 18 ml.

Figure 3:
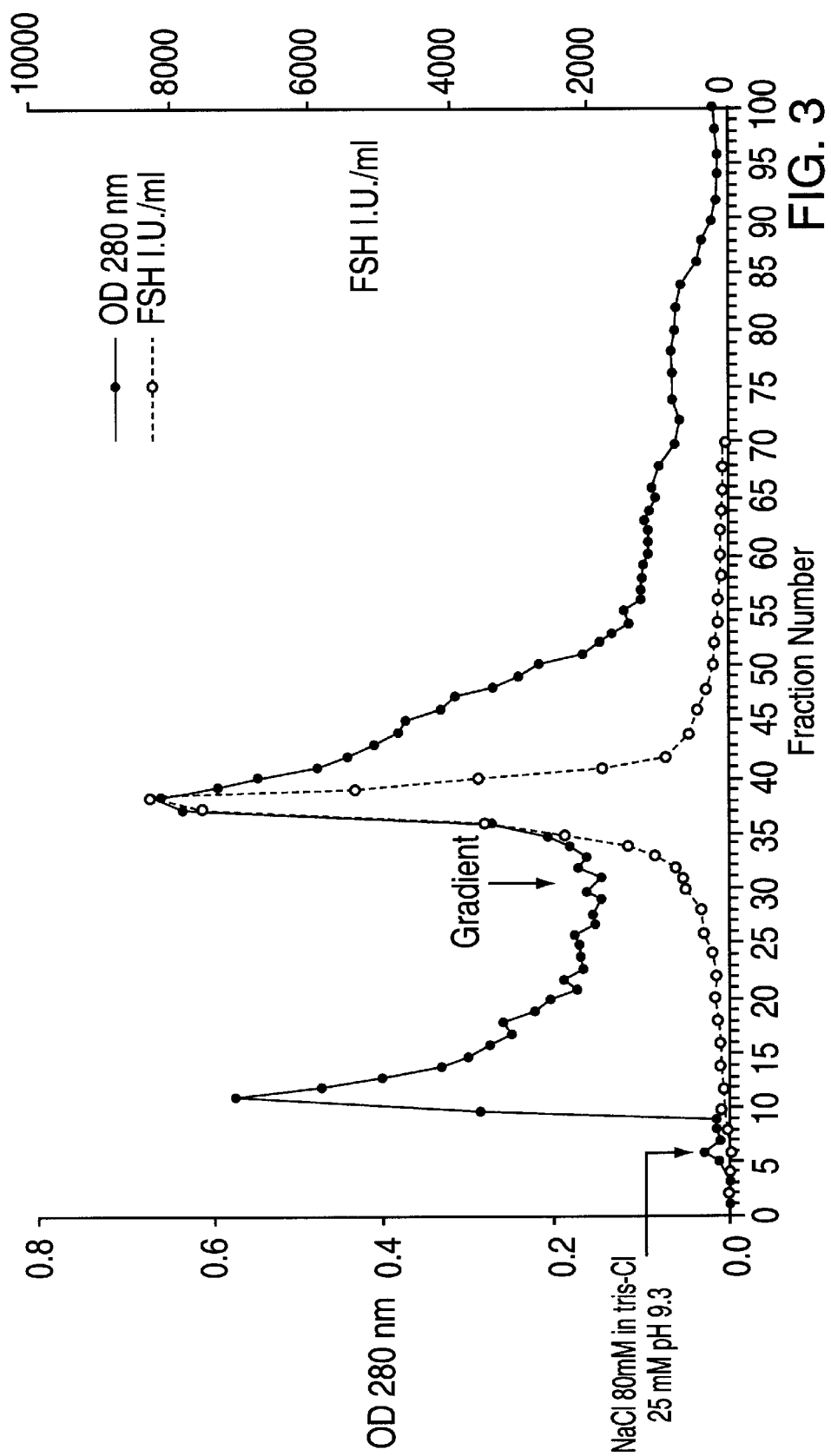

After sample loading, the column was first eluted, with 450 ml of a 25 mM Tris-HCl buffer, pH=9.3, containing 80 mM NaCl, and then with a NaCl linear gradient prepared as follows:

chamber 1) 600 ml of 90 mM NaCl in 25 mM Tris-HCl buffer, pH=9.3;

chamber 2) 600 ml of 160 mM NaCl in 25 mM Tris-HCl buffer, pH=9.3;

FIG. 3 shows the obtained chromatogram, where are reported the optical density at 280 nm (OD280), as well as FSH specific activity (I.U./ml) for each eluate fraction.

The chromatogram clearly shows that the washing with the first eluting solution, containing 80 mM NaCl, results into the elimination of some contaminating proteins, while FSH is still retained in the column. On the opposite, FSH is selectively eluted from contaminating proteins by means of the NaCl gradient, used from fraction 30 on. Fractions from 31 to 40 have been collected together, concentrated, desalified by using an Amicon cell equipped with an Amicon PM10 membrane, and finally lyophilized.

FSH Depyrogenation 109 mg of lyophilized FSH, obtained in previous step, were dissolved in 55 ml of a cold solution of 10% w/v ammonium acetate in 40% v/v ethanol. To the solution, maintained under magnetic stirring at a temperature of about $-10°$ C. by means of an ice and salt bath, the following ingredients were added:

1.2 ml of a 7.6% tribasic sodium phosphate dodecahydrate water solution;
  1.4 ml of a 4.9% calcium acetate water solution.

After having raised the pH up to about 8.5 by means of 20% w/v NaOH, the solution was maintained under stirring for 30 minutes, still at a temperature of about $-10°$ C., and then centrifuged at 8,000 rpm in a Sorvall SS34 rotor for 30 minutes. The precipitate was eliminated, while the collected supernatant (57 mm) was stirred and cooled down to about $-10°$ C. in an ice and salt bath.

After the addition of 114 ml of 95% v/v EtOH, previously cooled down to $-20°$ C., the solution was maintained under stirring for about 30 minutes and then left at rest for 12 hours, at the temperature of $-20°$ C.

After a 30 minute centrifugation at 8,000 rpm, in a 0–4° C. cooled centrifuge, the supernatant was eliminated and the precipitate was dissolved again in apyrogen water (80 ml). The thus obtained solution was dialyzed for 18 hours against 10 l of apyrogen water and then lyophilized.

Figure 4:
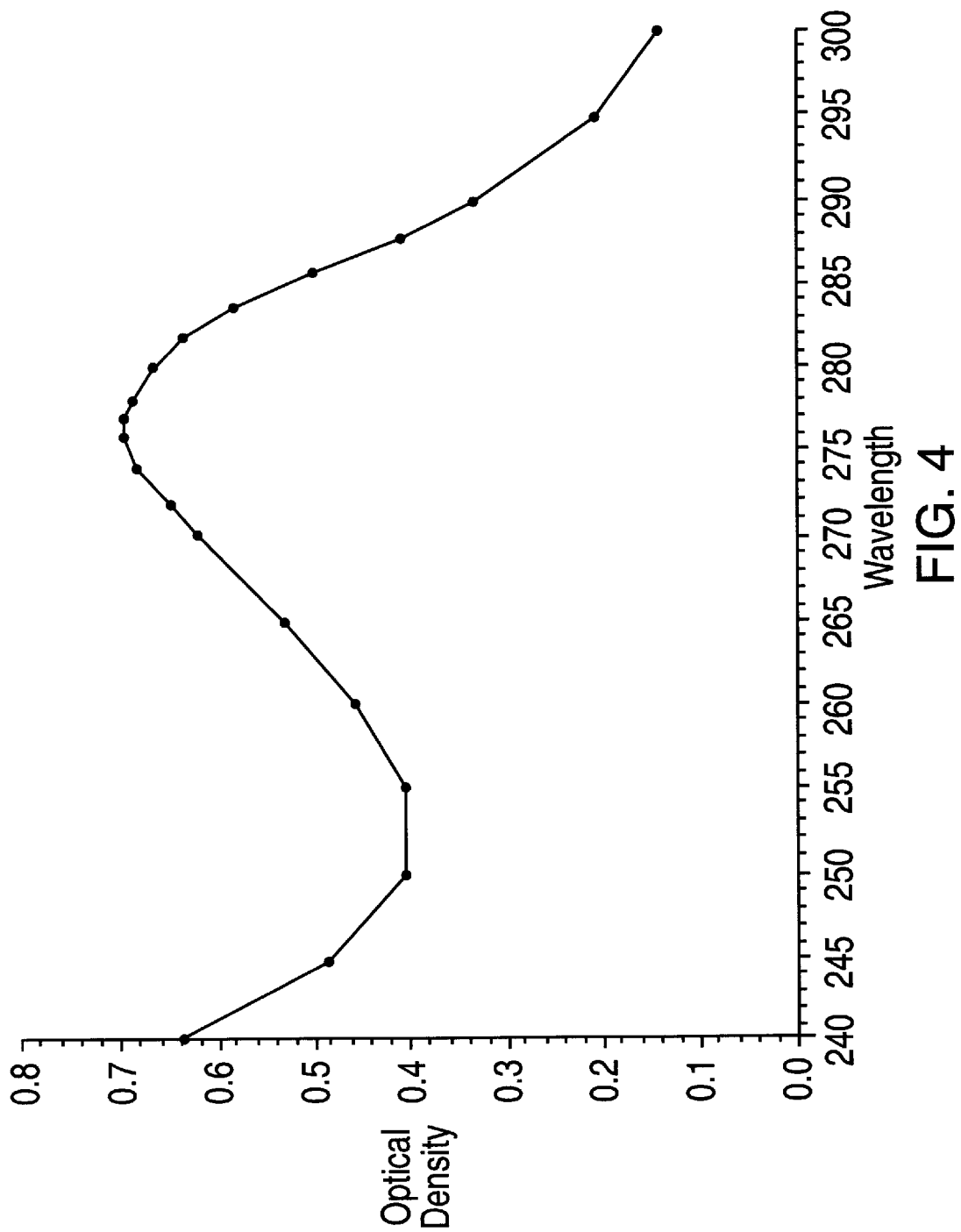

FIG. 4 shows the absorption sprectrum of a solution containing 1.1 mg/ml of FSH, purified according to the process reported above. The activity of the thus purified FSH, corresponding to 6,870 I.U./mg of proteins, was determined with an immunoradiometric method, using the Serono FSH Maicione kit (Cat. Ref. 13101). The protein concentration in purified FSH was calculated considering that a water solution containing 1 mg/ml of FSH produces an optical density of 0.62 at 277 nm, in quartz cuvettes with 1 cm optical path. Such coefficient was experimentally determined in the course of preparations, determining the absorption at 277 nm in solutions containing weighted quantities of previously lyophilized, salt-free hormone. Such coefficient proved to be more reliable than other protein determination methods in purified hormone samples with a specific activity in FSH ranging from 4,000 to 10,000 I.U./mg. The protein concentration of lower purity fractions (for example those obtained in step 1.2) were determined with BCA Protein Assay Pierce (Pierce catalogue ref. 23223 and 23224), using bovine serum albumine as standard.

Data referring to FSH purification, carried as described in steps 1.1–1.5, are shown in Table 1.

| Fraction | Volume (ml) | Total Proteins (mg) | Total FSH (I.U.) | Total LH (I.U.) | FSH specific activity (I.U./mg) | FSH/LH ratio |
|---|---|---|---|---|---|---|
| Solution from Step 1.1 | 2,200 | 195,000 | 1,384,000 | n.d. | 7.1 | n.d. |
| FSH from DE52 Step 1.2 | 9,700 | 18,516 | 1,148,600 | 27,000 | 62 | 43 |
| FSH from Agarose Blue Step 1.3 | 170 | 229 | 961,300 | 13,850 | 4,198 | 69 |
| FSH from DE53 Step 1.4 | 92 | 125 | 788,230 | 2,513 | 6,306 | 313 |
| Depyrogened FSH Step 1.5 | 99 | 109 | 748,780 | 2,572 | 6,870 | 291 |
| FSH from Step 1.5 after 2 months (−20° C.) | | 109 | 743,230 | n.d. | 6,818 | n.d. |
| FSH from Step 1.5 after 4 months (−20° C.) | | 109 | 741,640 | n.d. | 6,804 | n.d. |

Table 2 shows the results achieved in further FSH purification trials, carried out according to the methods described in Example 1.

| Fraction | Volume (ml) | Total Proteins (mg) | Total FSH (I.U.) | Total LH (I.U.) | FSH specific activity (I.U./mg) | FSH/LH ratio |
|---|---|---|---|---|---|---|
| Solution from Step 1.1 | 2,200 | 205,000 | 1,,50,000 | n.d. | 6.1 | n.d. |
| FSH from DE52 | 9,700 | 19,800 | 1,012,000 | 21,360 | 51 | 47 |

-continued

| Fraction | Volume (ml) | Total Proteins (mg) | Total FSH (I.U.) | Total LH (I.U.) | FSH specific activity (I.U./mg) | FSH/LH ratio |
|---|---|---|---|---|---|---|
| Step 1.2 FSH from Agarose Blue | 170 | 232 | 805,000 | 9,050 | 3,470 | 90 |
| Step 1.3 FSH from DE53 | 90 | 115 | 680,220 | 2,305 | 5,915 | 295 |
| Step 1.4 Depyrogened FSH | 87 | 97 | 631,620 | 2,110 | 6,511 | 299 |
| Step 1.5 FSH from Step 1.5 after 2 months (−20° C.) | | 97 | 630,450 | n.d. | 6,499 | n.d. |
| FSH from Step 1.5 after 4 months (−20° C.) | | 97 | 629,880 | n.d. | 6,494 | n.d. |

EXAMPLE 2

LH Purification from Crude Urinary HMG

Steps 2.1 and 2.2, referring to the exhaustion of crude HMG viral charge in aqueous EtOH and to ion-exchange chromatography on DE52, are common for both FSH and LH, and were carried out as described in items 1.1 and 1.2 of Example 1.

LH Purification by Affinity Chromatograohy on Agarose Blue

The agarose blue 3 GA affinity resin was prepared as described in item 1.3. It was then balanced in 20 mM sodium acetate buffer, pH=6.5, and packed into a chromatography column to obtain a resin bed with a diameter of 11 cm and a height of 16 cm.

The pH of the sample containing LH, obtained as described in item 1.2, was changed to 6.5 by means of 1.7 M acetic acid and said sample was loaded into the column with a flow rate of 1 l/h. The eiuate obtained during the sample loading in the column was collected in one single fraction, while further fractions of about 600 ml were subsequently collected.

After sample loading, the column was first eluted with, in the order:

1 l of a 20 mM sodium acetate buffer, pH=6.5;
5 l of a 50 mM glycine-NaOH buffer, pH=10;
2 l of a 50 mM glycine-NaOH, 0.15 M KCl buffer, pH=10;
and then with a KCl linear gradient in a glycine-NaOH buffer, prepared as follows:

chamber 1) 8 l of 0.15 M KCl in a 50 mM glycine-NaOH buffer, pH=10;
chamber 2) 8 l of 1.7 M KCl in a 50 mM glycine-NaOH buffer, pH=10.

After chromatography, the optical density at 280 nm (OD280) was determined for each fraction, as well as LH specific activity (I.U./ml).

Figure 5:
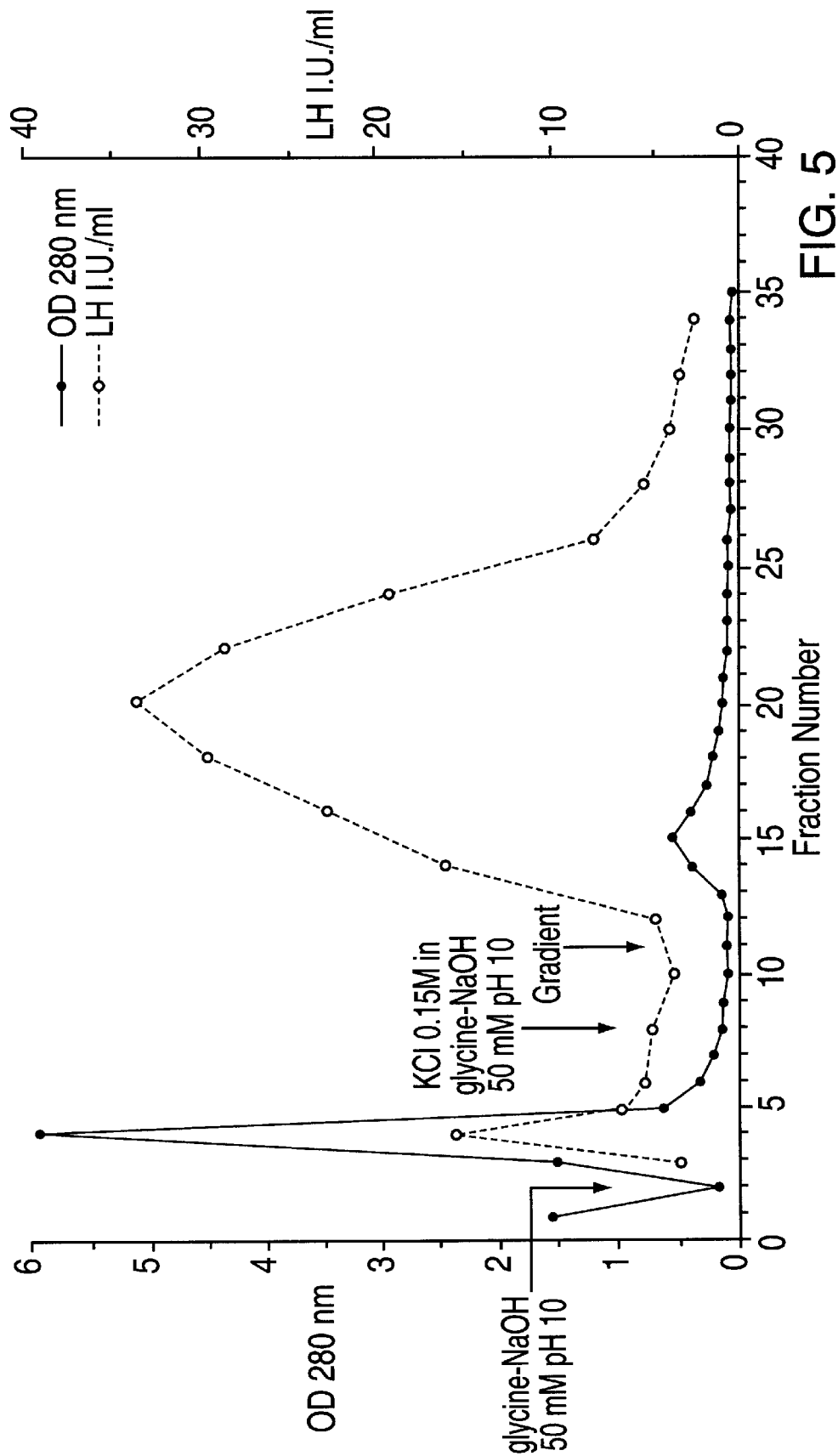

FIG. 5 shows the resulting elution chromatogram, obtained as described above. During sample loading into the column, LH was retained into the column, while the largest part of contaminating proteins was found in the eluate (not reported in the graphic). Many of the contaminating proteins retained by the resin were eluted by means of washings carried out with the two buffers at pH 10, before the gradient elution.

LH was eluted by the KCl gradient: low KCl concentrations resulted into the elution of further contaminating proteins, while LH elution occurred at higher ionic concentrations.

Fractions from 17 to 25 were then collected together and the pH value was changed to 7.5 with 1.7 M acetic acid. Then the solution was concentrated, desalified by ultrafiltration on an Amicon PM10 membrane and finally lyophilized.

LH Depyrogenation 205 mg of lyophilized LH, obtained in the previous step, were dissolved in 102 ml of a solution containing 40% v/v EtOH and 10% w/v ammonium acetate. To the solution, maintained under magnetic stirring at a temperature of about −10° C. by means of an ice and salt bath, the following ingredients were added:

2.25 ml of a 7.6% tribasic sodium phosphate dodecahydrate water solution;
2.7 ml of a 4.9% calcium acetate water solution.

After having raised the pH up to about 8.5 with 20% w/v NaOH, the solution was maintained under stirring for 30 minutes, at a temperature of about −10° C., and then centrifuged at 8,000 rpm in a Sorvall SS34 rotor, for 30 minutes. The precipitate was eliminated, while the collected supernatant (107 ml) was stirred, maintaining the temperature at about −10° C. in an ice and salt bath.

After the addition of 214 ml of 95% v/v EtOH, previously cooled down to −20° C., the solution was maintained under stirring for about 30 minutes and then left at rest for 12 hours, at the temperature of −20° C.

After a 30 minute centrifugation at 8,000 rpm, in a 0–4° C. cooled centrifuge, the supernatant was eliminated and the precipitate was dissolved again in apyrogen water (125 ml). The thus obtained solution was dialyzed for 18 hours against 10 l of apyrogen water and then lyophilized.

Figure 6:
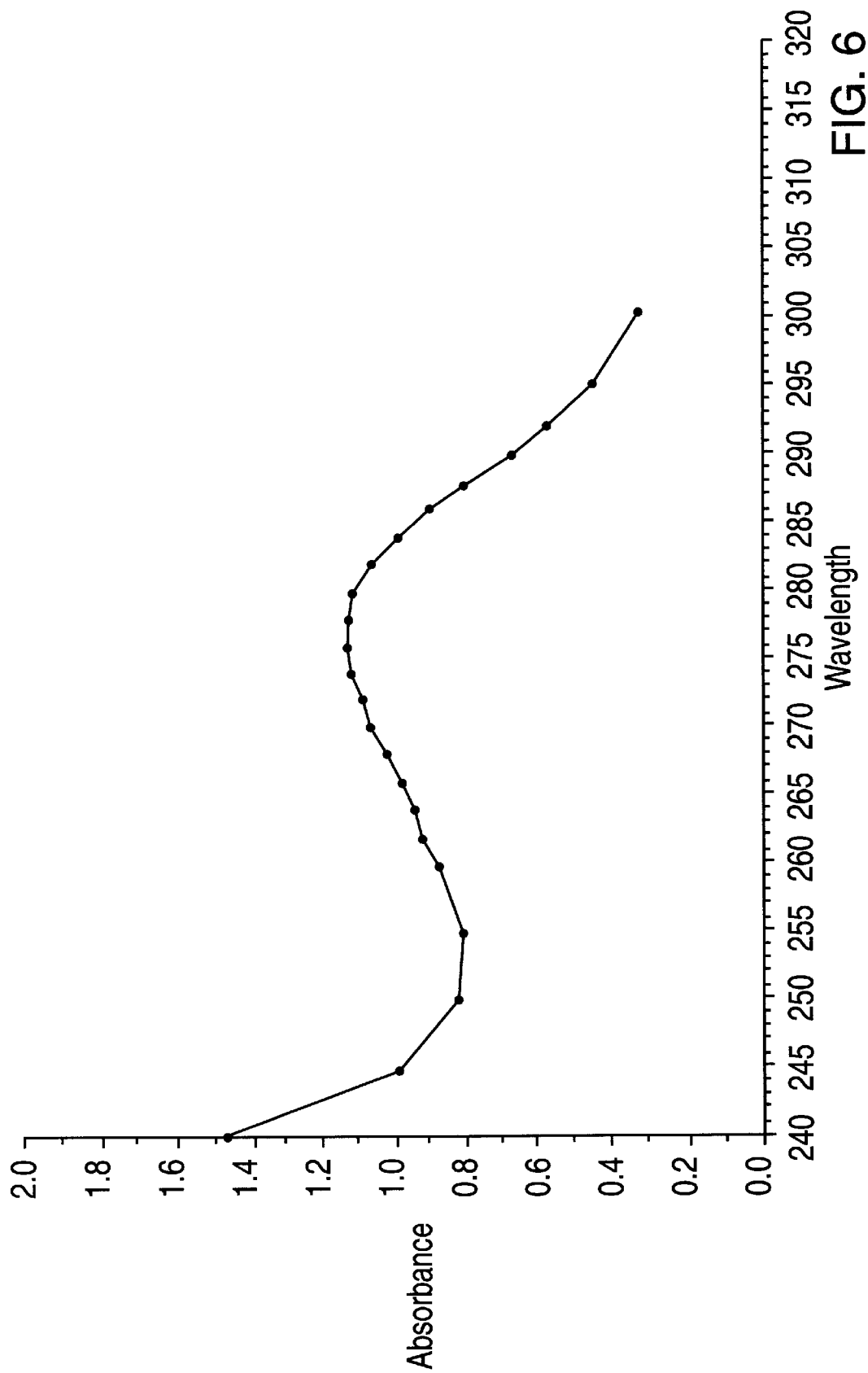

FIG. 6 shows the U.V. spectrum of an aqueous solution containing 2.8 mg/ml of LH, purified according to the process reported above. Purified LH specific activity, corresponding to 521 I.U./mg of proteins, was determined with immunoradiometric method, using the Serono LH Maiclone kit (Cat. Ref. 13201). The protein concentration was determined with BCA Protein Assay Pierce (Pierce catalogue ref. 23223 and 23224), using bovine serum albumin as standard.

Data corresponding to LH purification, carried out according to the above mentioned steps, are shown in Table 3.

| Fraction | Volume (ml) | Total Proteins (mg) | Total FSH (I.U.) | Total LH (I.U.) | LH specific activity (I.U./mg) | FSH/LH ratio |
|---|---|---|---|---|---|---|
| Solution from Step 1.1 | 2,200 | 195,000 | 1,384,000 | n.d. | n.d. | n.d. |
| LH from DE52 Step 1.2 | 10,700 | 8,970 | 30,400 | 171,500 | 19 | 0.18 |
| LH from Agarose Blue Step 2.3 | 190 | 307 | 21,280 | 117,000 | 381 | 0.18 |
| Depyrogened LH Step 2.4 | 125 | 205 | 19,600 | 106,800 | 521 | 0.18 |
| LH from Step 2.4 after 2 months (−20° C.) | | 205 | n.d. | 106,400 | 519 | n.d. |
| LH from Step 2.4 after 4 months (−20° C.) | | 205 | n.d. | 105,400 | 514 | n.d. |

Tabie 4 shows the results achieved in further LH purification trials, carried out according with methods described in Example 2.

| Fraction | Volume (ml) | Total Proteins (mg) | Total FSH (I.U.) | Total LH (I.U.) | LH specific activity (I.U./mg) | FSH/LH ratio |
|---|---|---|---|---|---|---|
| Solution from Step 1.1 | 2,200 | 205,000 | 1,250,000 | n.d. | n.d. | n.d. |
| LH from DE52 Step 1.2 | 10,600 | 11,785 | 18,400 | 165,000 | 14 | 0.11 |
| LH from Agarose Blue Step 2.3 | 110 | 260 | 10,700 | 105,600 | 406 | 0.1 |
| Depyrogened LH Step 2.4 | 120 | 185 | 9,470 | 97,800 | 529 | 0.1 |
| LH from Step 2.4 after 2 months (−20° C.) | | 185 | n.d. | 96,800 | 523 | n.d. |
| LH from Step 2.4 after 4 months (−20° C.) | | 185 | n.d. | 96,450 | 521 | n.d. |

What is claimed is:

1. A process of separation and purification of FSH and LH, starting from crude HMG, comprising the following steps:
   1) optional exhaustion of said crude HMG viral charge in a 80–90% v/v EtOH water solution;
   2) loading of the product obtained in step (1) on a ion-exchange chromatography column with weakly basic anionic resin of DEAE type, selectively eluting LH and FSH with 5–15% v/v EtOH water solutions in a 10–50 mM phosphate buffer, containing 0–70 mM NaCl at increasing ionic strength, at a pH of 7.0–8.0;
   3) loading of the eluate obtained in step (2), containing LH or FSH, in an affinity chromatography column having a CIBACRON® Blue (an anthraquinone derivative) as a ligand, selectively eluting contaminating proteins and FSH or LH with alkaline pH solutions, having an increasing ionic strength from 0 to 3 M of KCl;
   4) optional loading of FSH obtained in step (3) on an ion-exchange chromatography column packed with strongly basic anionic resins, selectively eluting the contaminating proteins and FSH with 0–400 mM NaCl solutions, with increasing ionic strength, at alkaline pH.

2. The process according to claim 1, wherein said crude HMG is obtained from the urine of menopausal or postmenopausal women.

3. The process according to claim 1, wherein, in step (1), said crude HMG is treated with said EtOH water solution at a temperature ranging from 20° C. to 5° C., for a time ranging from 1 to 4 hours.

4. The process according to claim 1, wherein, in step (2), said weakly basic anionic resin is DEAE cellulose.

5. The process according to claim 1 wherein, in step (2), said ion-exchange chromatography column is previously conditioned with a 5–15% v/v EtOH water solution in a 5–50 mM phosphate buffer, at a pH value of 7.3–7.6, at a temperature ranging from 0° C. to 8° C.

6. The process according to claim 1, wherein, in step (2), said LH is eluted from said column with a 5–15% v/v EtOH water solution containing 10–30 mM, sodium phosphate, pH 7.3–7.6, at a temperature ranging from 0° C. to 8° C.

7. The process according to claim 1, wherein, in step (2), said FSH is eluted from said column with a 5–15% v/v EtOH water solution containing 10–30 mM sodium phosphate and 30–50 mM sodium chloride, at a pH 7.3–7.6, at a temperature ranging from 0° C. to 8° C.

8. The process according to claim 1, wherein, in step (3), said affinity chromatography column consists of agarose blue.

9. The process according to claim 1, wherein, in step (3), said affinity chromatography column is previously conditioned with a 10–30 mM acetate buffer, at a pH of 5.5–7.5.

10. The process according to claim 1, wherein, in step (3), said LH or FSH is selectively eluted with one or more 40–60 mM glycine-NaOH buffers, containing KCl in concentrations ranging from 0 to 3 M, changing the pH value from 8.5 to 11.

11. The process according to claim 1, wherein, in step (4), said strongly basic anionic resin contains quaternary ammonium groups on cellulose matrix.

12. The process according to claim 1, wherein, in step (4), said ion-exchange chromatography column is previously conditioned with 10–50 mM Tris-HCl buffer, at a pH of 9.0–9.5.

13. The process according to claim 1, wherein, in step (4), said contaminating proteins are eluted with a 10–50 mM Tris-HCl buffer containing 40–80 mM NaCl, at a pH of 9.0–9.5 and that said FSH is selectively eluted from contaminating proteins with a NaCl gradient, whose concentration ranges from 70 to 400 mM, in a 10–50 mM Tris-HCl buffer, pH 9.0 to 9.5.

14. The process according to claim 1, wherein, said FSH or LH, obtained in step (3) or (4), is subsequently lyophilized or frozen, and depyrogened.

* * * * *